United States Patent

Denton et al.

[11] Patent Number: 5,850,917
[45] Date of Patent: Dec. 22, 1998

[54] SYRINGE DOSAGE TRACKING DEVICE WITH COOLING FEATURE

[76] Inventors: George D. Denton; Laura M. Denton, both of 1717 Amber Leaf Way, Lodi, Calif. 95242

[21] Appl. No.: 779,967

[22] Filed: Dec. 23, 1996

[51] Int. Cl.⁶ .......................... B65D 85/20; B65D 85/42; F25D 3/08
[52] U.S. Cl. .......................... 206/366; 62/371; 62/457.9; 206/370; 206/443; 211/60.1; 211/85.13
[58] Field of Search ................ 211/60.1, 85.13, 211/70.6; 206/364–366, 564, 459.5, 438, 370, 571, 562, 446, 443; 62/457.1, 457.9, 371

[56] References Cited

U.S. PATENT DOCUMENTS

| | | | |
|---|---|---|---|
| 1,650,980 | 11/1927 | Campbell | 206/366 |
| 3,300,855 | 1/1967 | Rohr | 206/564 X |
| 4,195,734 | 4/1980 | Boner et al. | 206/564 X |
| 4,250,998 | 2/1981 | Taylor | 206/570 |
| 4,349,338 | 9/1982 | Heppler | 206/459.5 X |
| 4,657,138 | 4/1987 | Watson . | |
| 4,658,957 | 4/1987 | Guth et al. | 206/365 |
| 4,850,484 | 7/1989 | Denman | 206/366 |
| 4,863,451 | 9/1989 | Marder | 206/366 X |
| 4,932,533 | 6/1990 | Collier | 206/370 X |
| 5,249,680 | 10/1993 | Shillington | 206/366 |
| 5,285,896 | 2/1994 | Salatka et al. | 206/366 |
| 5,311,985 | 5/1994 | Suida . | |
| 5,396,989 | 3/1995 | Hein | 206/366 |
| 5,464,348 | 11/1995 | Fischer et al. . | |
| 5,704,223 | 1/1998 | MacPherson et al. | 62/457.9 X |

*Primary Examiner*—Bryon P. Gehman
*Attorney, Agent, or Firm*—John P. Costello

[57] ABSTRACT

A syringe holder and dosage tracking device comprised of a base member having at least one, and preferably, a plurality of cavities imparted therein. Time indicia are placed near the cavities to designate an interval of time for which a syringe dosage should be administered. Medication-filled syringes are placed in the cavities and administered according to an interval of time being reached. This device may also incorporate a needle severing device to reduce the risk of injury from contaminated needles, following use. The needle severing device is in communication with a storage means, wherein severed needles and syringe bodies can be stored following use, and prior to disposal.

1 Claim, 2 Drawing Sheets

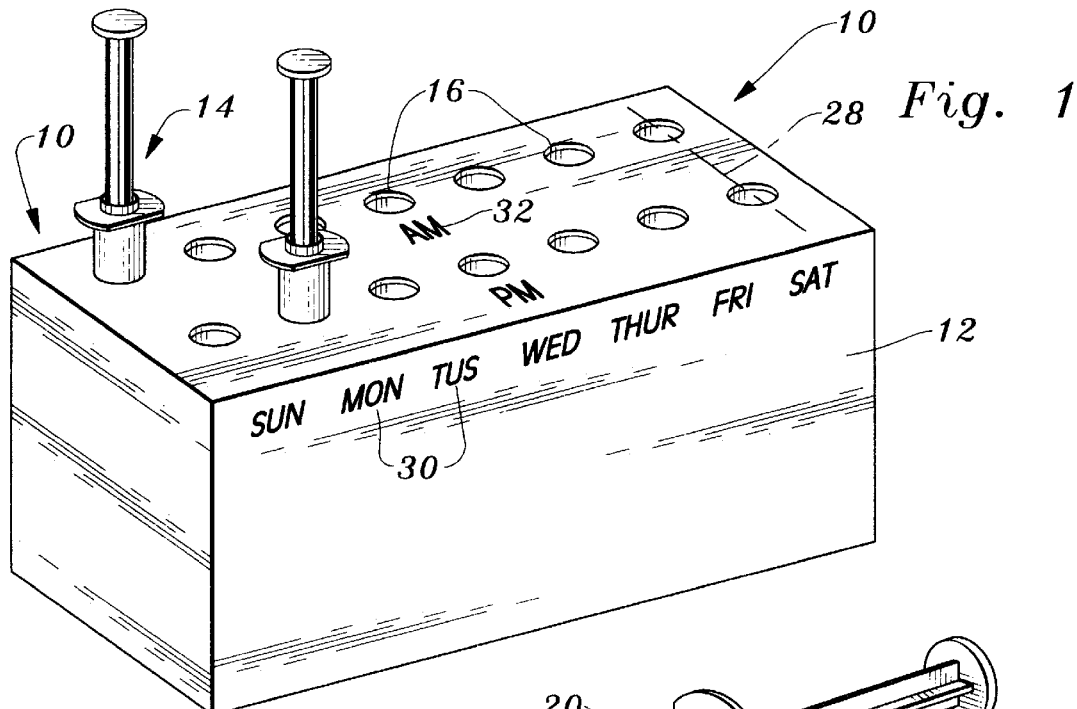
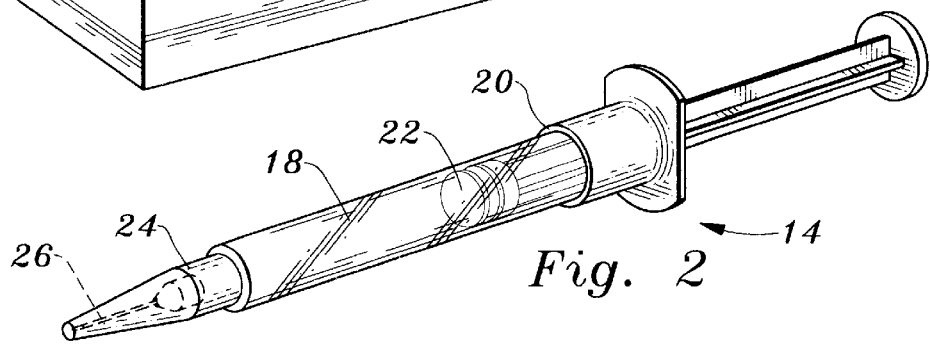
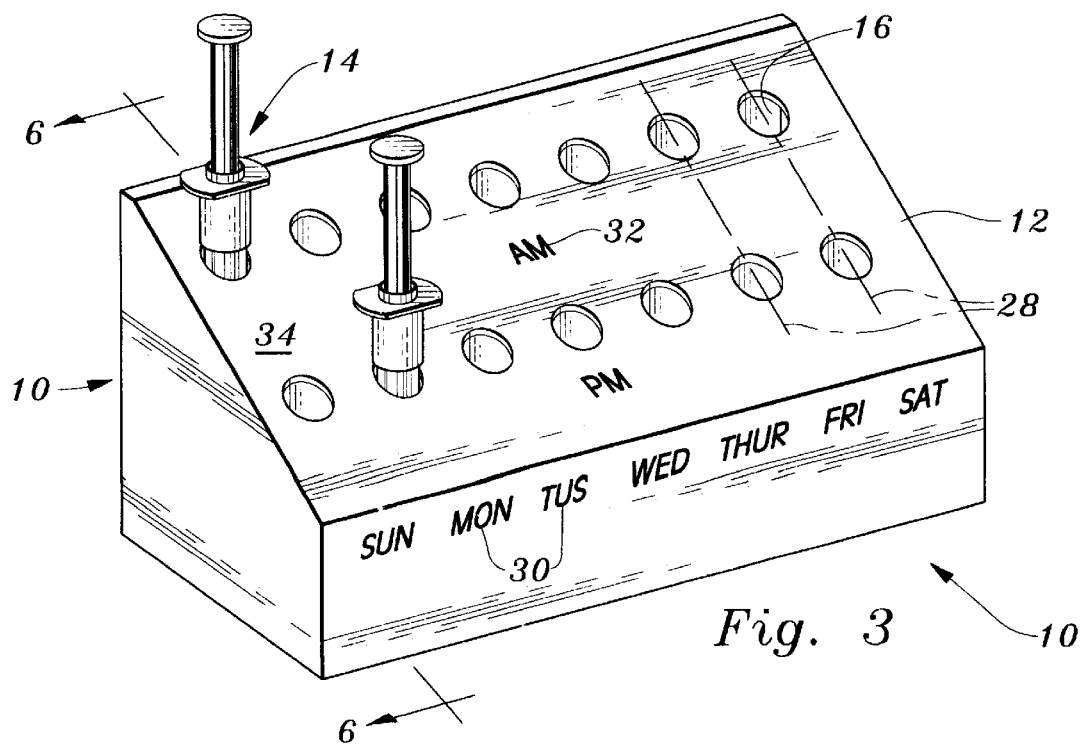

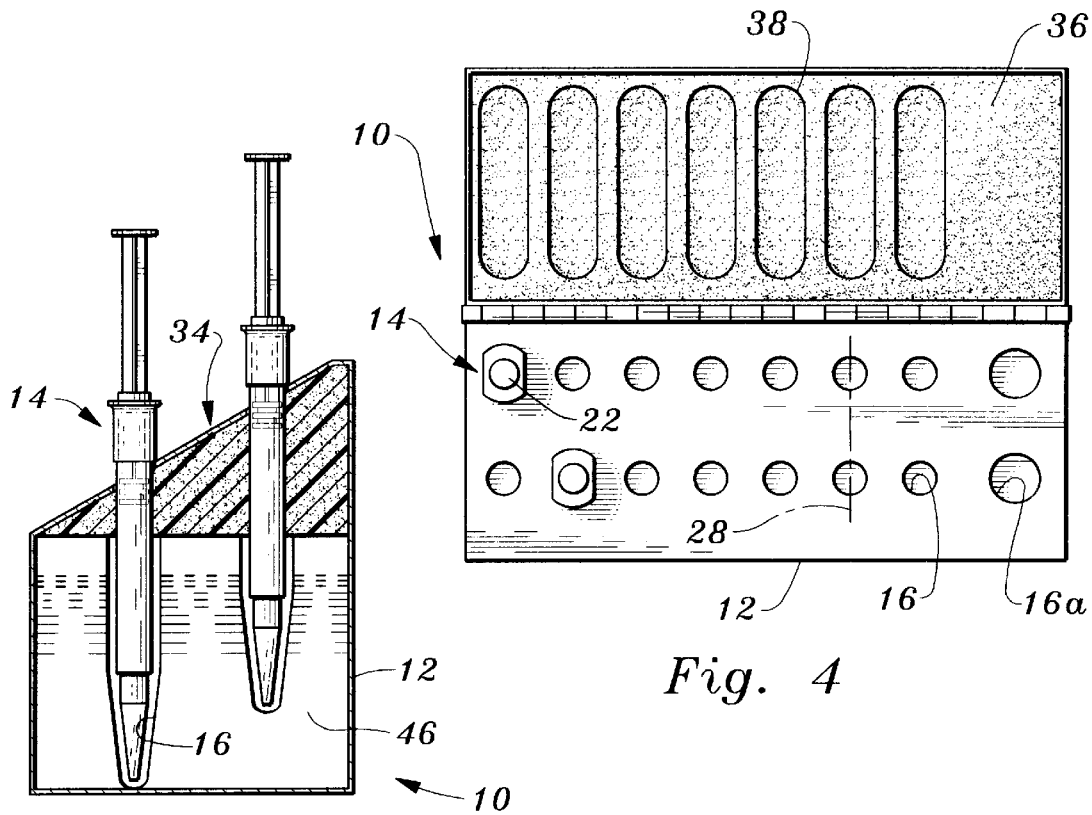
Fig. 4
Fig. 6
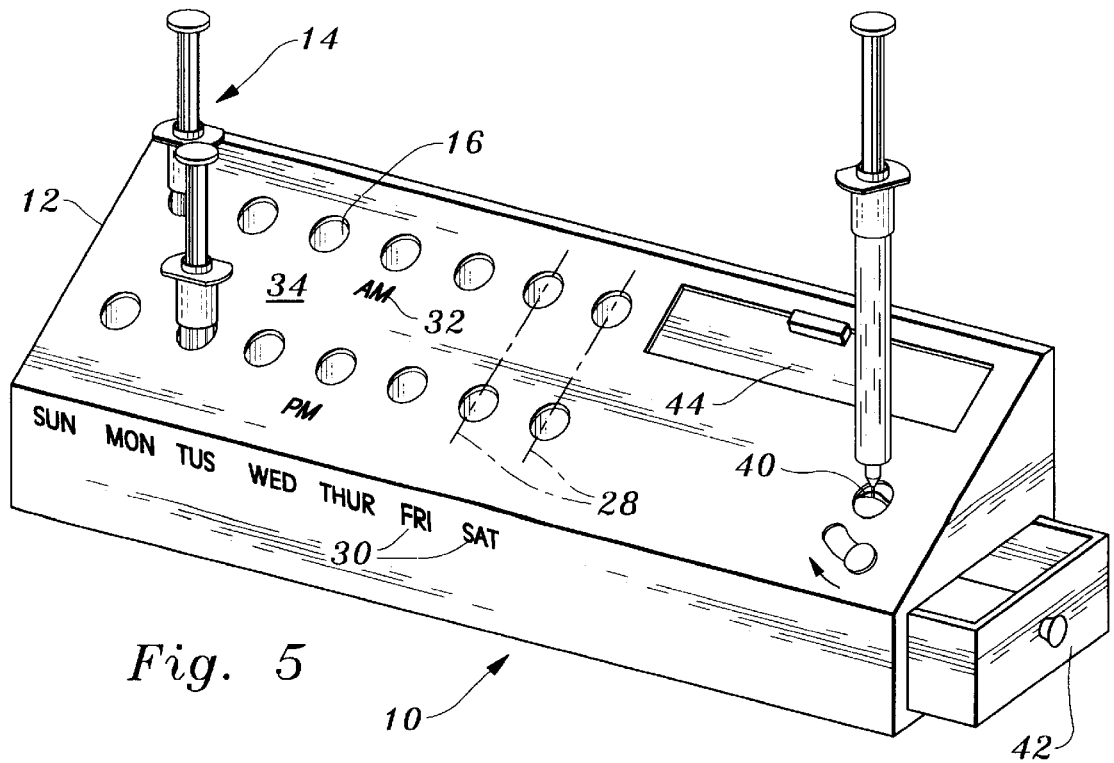
Fig. 5

SYRINGE DOSAGE TRACKING DEVICE WITH COOLING FEATURE

BACKGROUND OF THE INVENTION

1. Field of the Invention

This invention pertains to a device for holding a quantity of syringes and, more specifically, to a device for holding syringes in an ordered manner corresponding to intervals of time required for delivering a dosage of medication.

2. Description of the Background Art

Medication is commonly delivered in specified dosages during different intervals in time. For example, a patient's physician might order the patient to take a specified quantity of pills twice a day, e.g. one specified quantity in the morning and one specified quantity at night. Additionally, these dosage regimens can be even more rigorous, for example, in cases where a patient is required to administer a specified dosage on an hourly basis.

A common problem occurs when a patient forgets to take his required medication, at a required interval in time. This problem becomes more prevalent as the number of times required for dosages is increased. Often the patient forgets whether a dosage was taken, when in fact it was, and instead, ends up taking a double dosage, which can have a deleterious effect, especially with strong medications.

To avoid forgetting to take dosages, numerous solutions have been devised. With regard to pill dosages, a device commonly known as a "pill-minder" has been developed, which is comprised of a plurality of compartments for containing pills, each compartment containing date and time indicia for allowing a patient to keep track of his dosages. The compartments on the pill-minder often are covered with snap-fit lids which allow the pills to be safely contained prior to use.

However, the pill-minder has no means for accommodating syringes, and is therefore not useful for containing syringe-administered medications, such as insulin. Prior art devices of which the inventor is aware include holders for syringes, such as that disclosed in U.S. Pat. No. 5,464,348, issued to Fischer et al. However, this device does not include date and time indicia for ordering syringes according to specified intervals of time, for dosage purposes.

Another example is the holder for hypodermic needles described in U.S. Pat. No. 5,311,985, issued to Suida. This device is adapted for safely holding hypodermic needles only, and therefore, has little utility for holding an entire syringe, or for administering timed dosages of medication.

Carrying cases for insulin syringes, of the type seen in U.S. Pat. No. 4,657,138, issued to Watson, allow a diabetic to carry a plurality of filled insulin syringes, as well as a spare bottle of insulin. However, while such a carrying case provides convenience, it still does not incorporate time indicia for keeping track of syringe dosages.

While the prior art cited herein does not adequately provide a means for reliably tracking syringe dosages, additional considerations for syringe users have also been overlooked. Specifically, used syringes present a health hazard relating to needle pricks, and the like, which can result in the transmission of diseases such as Acquired Immune Deficiency Syndrome (AIDS), or hepatitis. Therefore, it would be desirable for a device which tracks and stores syringe dosages to have a means for disposing of used hypodermic needles. Additionally, many modern syringe medications are affected adversely by high temperatures, and, therefore, it would also be desirable for a device which stores and tracks syringe dosages to incorporate a cooling means for cooling the syringes. Such a feature would prevent degradation of the medication during storage in a hot vehicle, for example.

Accordingly, the foregoing patents and other information reflects the state of the art of which the inventor is aware, and is tendered with a view toward discharging the inventor's acknowledged duty of candor in disclosing information which may be pertinent with regards to the patentability of the present invention. It is respectfully stipulated, however, that the disclosed information does not teach or render obvious, singly or when considered in combination, the inventor's claimed invention.

SUMMARY OF THE INVENTION

By way of example, and not of limitation, the present invention generally pertains to a device for storing a plurality of syringes and tracking dosages delivered from each of a plurality of syringes. This device includes time indicia placed in corresponding relation to each of said plurality of syringes. In this manner, a syringe medication user can track the dosages administered from each syringe so that dosages are not missed, or so that double dosages are not delivered, during a specified time interval.

In one embodiment of the invention, a base member is provided, wherein a plurality of cavities are placed therein, in a specified order, corresponding to specified time intervals. The cavities provide a means for placing a single syringe in a substantially immobile state, and time indicia are placed in a corresponding relation to each cavity to define intervals in time for which a corresponding syringe dosage should be administered. More specifically, if a dosage regimen includes twice-daily syringe dosages to be administered, for example, then a row having two cavities, one for an A.M dosage and one for a P.M. dosage, could be arranged. Even more specifically, each row of cavities could include indicia denoting a day of the week, wherein seven rows would correspond to seven days. The number of cavities in each row is not limited, and can correspond to any required dosage regimen, which might require dosages to be administered on an hourly basis, for example.

In a second embodiment, the base member is provided with an angled face for purposes of allowing a syringe user to easily view the indicia corresponding to each syringe dosage, at a glance.

In a third embodiment, the device is provided with a closeable lid.

In a fourth embodiment, the base member is provided with a means for severing a hypodermic needle from its corresponding syringe body for purposes of safely disposing of contaminated needles. Additionally, this embodiment can be provided with a storage means for placing used needles and syringe bodies.

In a fifth embodiment, the base member is provided with a cooling means for cooling the medication which is stored in the syringes. This feature would allow the device to be safely stored in a hot automobile, during travel, for example.

Accordingly, this invention will be more fully understood through the following objects and advantages:

An object of the invention is to provide a device for storing syringes and tracking dosages administered from each syringe.

Another object of the invention is to provide a syringe storing and tracking device with a means for safely disposing of used hypodermic needles and syringes.

Still another object of the invention is to provide a syringe storing and tracking device with a means for cooling temperature-sensitive medications.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings which are for illustrative purposes only:

FIG. 1 is a perspective view of a first embodiment of the syringe storing and tracking device which is the present invention, this embodiment having a flattened face.

FIG. 2 is a side perspective view of a typical syringe having a covered needle which would be used with the invention.

FIG. 3 is a perspective view of a second embodiment of the syringe storing and tracking device, this embodiment having an angled face.

FIG. 4 is a plan view of a third embodiment of the syringe storing and tracking device, shown with a closeable lid and added storage for bottles of medication.

FIG. 5 is an elevated perspective view of a fourth embodiment of the syringe storing and tracking device shown with a means for severing hypodermic needles, which incorporates storage means for storing severed needles and used syringe bodies.

FIG. 6 is a side cutaway view of a fifth embodiment of the syringe storing and tracking device, incorporating a means for cooling the device.

DESCRIPTION OF THE PREFERRED EMBODIMENTS

Referring more specifically to the drawings, the syringe storage and tracking device which is the present invention, is shown generally in FIG. 1. The device 10 includes a base member 12 for ordering a dosage regimen of syringe-delivered medication. Base member 12 could be of any dimension and shape, with the main requirement being that it be capable of ordering syringes according to specified intervals of time. Syringes 14 are preferably ordered in base member 12 by being placed in a plurality of cavities 16, imparted therein. Base member 12 may be constructed from a plurality of materials, plastics being preferred for ease of molding and manufacture.

Cavities 16 are preferably sized to fit the diameters of standard syringes 14, such as those used to administer insulin. FIG. 2, illustrates a typical syringe 14 having a syringe body 18, a flange 20, a plunger 22, and a cover 24 for a sterile hypodermic needle 26.

Additionally, cavities 16 can include a lining made of foam or other flexible material so that syringes having different diameters could be accommodated. The foam or other flexible material would "give", according to the diameter of the syringe 14 placed in cavities 16, and be fitted snugly therein. Cavities 16 are preferably of a depth which allows a syringe 14 having a covered hypodermic needle 26, to be sunk into cavity 16 up to flange 20. Positioning syringes 14 deep inside of cavities 16 represents the best arrangement for safely storing loading and transporting syringes 14 in device 10.

Cavities 16 are arranged in rows 28 which correspond to a dosage regimen. A date indicia 30 is preferably placed at the head of one or more rows to designate a day's dosage regimen. Corresponding with each cavity 16, time indicia 32 are preferably placed to designate an interval in time for which a syringe dosage should be delivered. Time indicia 32 could designate A.M. and P.M., hourly, or other time intervals.

Referring to FIG. 3, a second embodiment of the invention which incorporates the features heretofore described, and additionally, comprises an angled face 34, is shown. Angled face 34 allows a syringe user to easily view the time and date indicia, at a glance, because the indicia 30, 32 are brought to bear at a preferred orientation for a viewer's line of sight.

FIG. 4 depicts a third embodiment of the invention which incorporates the features heretofore described, and additionally, comprises a closeable lid 36 and an added cavity 16a for storing a bottle of medication, such as insulin. Closeable lid 36 is preferably lined with a depressible material, such as foam 38, which contacts the tops of plungers 22 upon closing lid 36, so that syringes 14 are held fast within device 10, during transport.

FIG. 5 illustrates a fourth embodiment of the invention which is useful for safely disposing of used hypodermic needles. This embodiment incorporates the features heretofore described, and additionally, comprises a needle severing means 40 and storage means 42 for storing severed needles 26 and used syringe bodies 18. Needle severing means 40 can be, for example, of a needle shears type, already in common use, or merely be a cavity having a diameter slightly larger than the needle's diameter, thereby allowing for the needle to break when it is mechanically applied against the cavity walls. Storage means 42 can be a compartment or drawer receptacle in communication with the needle severing means 40. If a drawer receptacle is used, the severed needles and syringe bodies would preferably fall into the drawer, which could subsequently be pulled out of base member 12 for sanitary disposal. Additionally, an opening, such as a sliding door 44 can be incorporated into base member 12 to allow for a syringe body 18 to be dropped into the storage means 42. Also, if a drawer receptacle is used as a storage means, it is preferable that the drawer be equipped with a locking means to prevent the drawer from inadvertently opening when base member 12 is transported from a first, to a second location.

Finally, in FIG. 6, a fifth embodiment of the invention is shown. This embodiment incorporating means for cooling syringes 14 placed in cavities 16. Cooling means 46 is preferably self-contained within base member 12 and also surrounds cavities 16. A cooling means which would meet the requirements of the invention would be for example, water, or an electrolyte composition commonly referred to as "blue ice". In the case of using water as a cooling means, the base member would be hollow, and modified to have a fill hole, to allow water to enter and exit. The cavities 16 would also depend down into the hollow base member 12 to allow frozen water to surround them, upon freezing. In the case of using blue ice, it would be permanently contained within the hollow base member 12, at the time of manufacture. Whether water or blue ice is used, the entire device 10 would be placed in a freezer. Upon being frozen, syringes 14 having temperature-sensitive medication therein could be placed into cavities 16 and the medication could remain cool during transport in a hot automobile, for example.

In use, device 10 allows a syringe user to accurately track his dosage regimen according to the time and date indicia means 30, 32 imparted onto the face of device 10. Device 10 can be manufactured according to the dosage needs of specific syringe users. For example, most diabetics require a morning and night dosage of insulin, and therefore, rows 28 need only have two cavities, for the majority of diabetics. For other medical conditions, additional rows 28, cavities 16, and indicia means 30, 32, could be added to tailor device 10 to a particular medical condition.

Finally, although the description above contains many specificities, these should not be construed as limiting the scope of the invention, but as merely providing illustrations of some of the presently preferred embodiments of this invention. Thus the scope of this invention should be determined by the appended claims and their legal equivalents.

We claim:

1. A medication syringe holder, the holder comprising:
    a) a base member for placing a plurality of syringes in an ordered relation corresponding to a dosage regimen to be delivered in a defined interval of time, said base member having an angled face portion;
    b) a plurality of cavities imparted into said angled face portion, said cavities for ordering a corresponding plurality of syringes;
    c) indicia means for indicating an interval in time required for the delivery of a syringe dosage, said indicia means being placed upon said angled face portion at a corresponding location near said cavities;
    d) severing means for severing a syringe needle from a corresponding syringe body, said severing means being positioned upon said angled face portion;
    e) a removable storage means for removably storing a quantity of severed syringe needles within said base member, said removable storage means being in communication with said severing means for purposes of readily accepting a quantity of severed syringe needles;
    f) a closeable lid in communication with said base member for enclosing a plurality of syringes located in said cavities; and
    g) means for filling said base member with a fluid cooling means for surrounding said cavities within said base member and cooling a quantity of syringes positioned in said cavities.

* * * * *